United States Patent
Gregorius et al.

(10) Patent No.: US 11,879,027 B2
(45) Date of Patent: Jan. 23, 2024

(54) MOLECULAR IMPRINTED POLYMERS TARGETING PHENYLALANINE

(71) Applicant: Mipsalus ApS, Hørsholm (DK)

(72) Inventors: Klaus Gregorius, Søborg (DK); Nicolas Otto Krogh, Virum (DK)

(73) Assignee: MIPSALUS APS, Hørsholm (DK)

( * ) Notice: Subject to any disclaimer, the term of this patent is extended or adjusted under 35 U.S.C. 154(b) by 193 days.

(21) Appl. No.: 17/317,033

(22) Filed: May 11, 2021

(65) Prior Publication Data

US 2021/0277158 A1 Sep. 9, 2021

Related U.S. Application Data

(62) Division of application No. 16/624,578, filed as application No. PCT/EP2018/067539 on Jun. 29, 2018, now Pat. No. 11,028,203.

(30) Foreign Application Priority Data

Jun. 29, 2017 (EP) .................................... 17178745

(51) Int. Cl.
| | | |
|---|---|---|
| *A61K 31/787* | (2006.01) | |
| *C08F 220/18* | (2006.01) | |
| *A61K 9/00* | (2006.01) | |
| *C08F 2/22* | (2006.01) | |
| *C08F 2/32* | (2006.01) | |
| *C08F 226/06* | (2006.01) | |
| *B01J 20/26* | (2006.01) | |
| *C07K 1/22* | (2006.01) | |
| *C07K 5/06* | (2006.01) | |
| *C07K 5/08* | (2006.01) | |

(52) U.S. Cl.
CPC .......... *C08F 220/18* (2013.01); *A61K 9/0053* (2013.01); *A61K 31/787* (2013.01); *B01J 20/268* (2013.01); *C08F 2/22* (2013.01); *C08F 2/32* (2013.01); *C08F 226/06* (2013.01); *C07K 1/22* (2013.01); *C07K 5/06* (2013.01); *C07K 5/08* (2013.01)

(58) Field of Classification Search
None
See application file for complete search history.

(56) References Cited

U.S. PATENT DOCUMENTS

| 9,212,271 B2 * | 12/2015 | Gregorius | B01D 15/3804 |
| 2009/0123411 A1 | 5/2009 | Bay-Oudh et al. | |

FOREIGN PATENT DOCUMENTS

| CN | 1718593 A | 1/2006 | |
| CN | 104168998 A | 11/2014 | |
| CN | 106317335 A | 1/2017 | |
| WO | WO 95/01347 A1 | 1/1995 | |
| WO | WO 2007/004197 A2 | 1/2007 | |
| WO | WO 2007/004197 A3 | 1/2007 | |
| WO | WO 2007/095949 A2 | 8/2007 | |
| WO | WO 2011/033021 A2 | 3/2011 | |
| WO | WO 2011/033021 A3 | 3/2011 | |
| WO | WO 2011/071447 A1 | 6/2011 | |
| WO | WO-2011071447 A1 * | 6/2011 | .......... A61M 1/3673 |
| WO | WO 2013/127433 A1 | 9/2013 | |
| WO | WO 2017/157980 A1 | 9/2017 | |

OTHER PUBLICATIONS

Najafizdeh et al., J Mater Chem B, 2014, vol. 2, pp. 2144-2152 (Year: 2014).*
Chen et al., "Molecular imprinting: perspectives and applications," Chemical Society Reviews, 45(8):2137-2211, (2016).
Morelli et al., "Molecularly imprinted submicronspheres for applications in a novel model biosensor-film," Sensors and Actuators B, 150(1): 394-401, (2010).
O'Shannessy et al., "Molecular Imprinting of Amino Acid Derivatives at Low Temperature (0° C.) Using Photolytic Homolysis of Azobisnitriles," Analytical Biochemistry, 77(1):144-149, (1989).
Piletsky et al., "Combined Hydrophobic and Electrostatic Interaction-Based Recognition in Molecularly Imprinted Polymers," Macromolecules, 32(3):633-636, (1999).
Shah et al., "Highly improved adsorption selectivity of L-phenylalanine imprinted polymeric submicron/nanoscale beads prepared by modified suspension polymerization," Korean Journal of Chemical Engineering, 28(9): 1936-1944, (2011).
Yan et al., "Characteristics and synthetic approach of molecularly imprinted polymer," Int. J. Mol. Sci, 7(5):155-178, (2006).
PCT/EP2018/067539, International Preliminary Report on Patentability dated Sep. 12, 2019.
PCT/EP2018/067539, International Search Report and Written Opinion dated Oct. 18, 2018.
PCT/EP2018/067539, Written Opinion of the International Preliminary Examining Authority dated May 27, 2019.
U.S. Appl. No. 16/624,578, filed Dec. 19, 2019, U.S. Pat. No. 11,028,2013, Allowed.
CN Application No. 201880040008.7, Office Action dated Aug. 9, 2022.
JP Application No. 2019-572052, Notice of Reasons for Refusal dated Jun. 14, 2022.
Najafizadeh, P, et al., "Synthesis of a phenylalanine imprinted polymer for attenuation of phenylalanine absorption via the gut in a murine hyperphenylalaninemia model," *Journal of Materials Chemistry B*, 2014, vol. 2, pp. 2144-2152.

* cited by examiner

*Primary Examiner* — Brian Gulledge
(74) *Attorney, Agent, or Firm* — Womble Bond Dickinson (US) LLP

(57) ABSTRACT

Disclosed is agents and methods that target metabolism malfunctions, inborne as well as acquired, as well as methods for preparation of the agents. In particular, the invention relates to methods for preparing molecular imprinted polymers with high binding capacity for phenylalanine or tyrosine, MIPs that bind phenylalanine or tyrosine, and methods for treating phenylketonuria, alkaptonuria, and hypertyrosinemia.

10 Claims, 1 Drawing Sheet

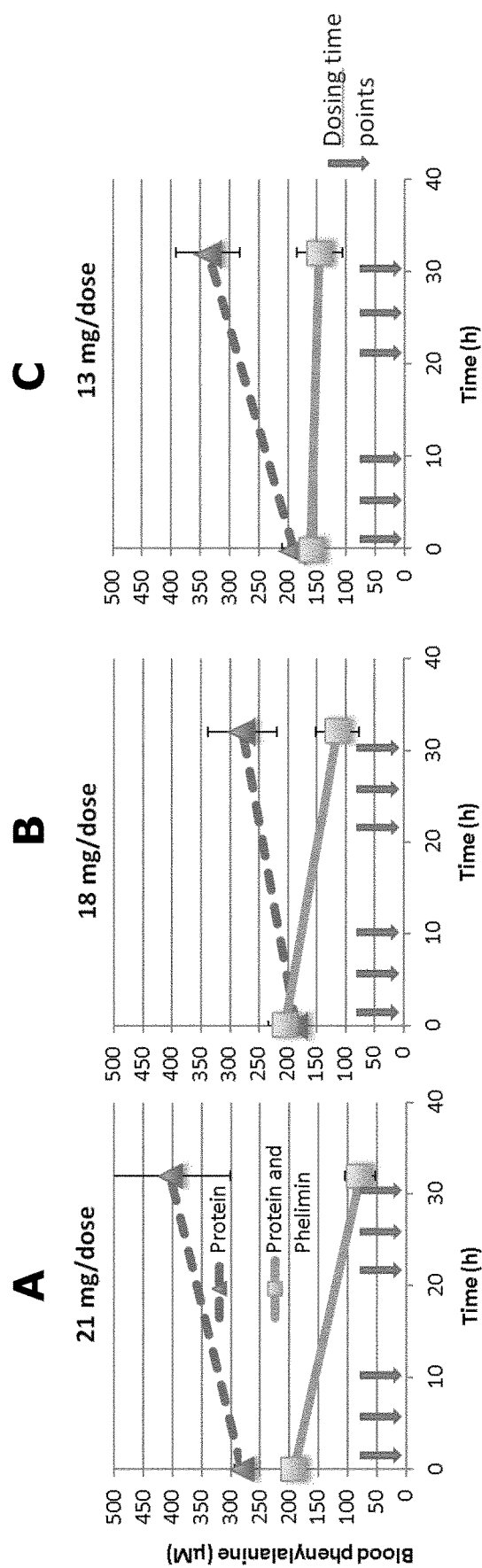

MOLECULAR IMPRINTED POLYMERS TARGETING PHENYLALANINE

RELATED APPLICATIONS

This application is a divisional of U.S. application Ser. No. 16/624,578, filed Dec. 19, 2019, which is a national stage application of PCT/EP2018/067539 filed Jun. 29, 2018, which claims priority to EP Application No. 17178745.0, filed Jun. 29, 2017, the entirety of each of which are incorporated herein by reference.

FIELD OF THE INVENTION

The present invention relates to agents and methods that target metabolism malfunctions, inborne as well as acquired, as well as methods for preparation of the agents. In particular, the invention relates to methods for preparing molecular imprinted polymers with high binding capacity for phenylalanine or tyrosine, MIPs that bind phenylalanine or tyrosine, and methods for treating phenylketonuria, alkaptonuria, and hypertyrosinemia.

BACKGROUND OF THE INVENTION

Previously, the present inventors have provided methods for preparation of molecular imprinted polymers (MIPs) that provide for hitherto unseen capacities for binding by the resulting MIP compositions. In this way, the inventors have provided novel treatments of certain metabolism malfunctions that it has not previously been possible to address with medicinal products: for instance, treatment of phenylketonuria by daily administration of high-capacity MIPs that confine phenylalanine to the gastrointestinal tract has been a major advance. Another advantage of the improved MIPs obtained by these methods are their use in highly sensitive assays.

The technologies that found the basis of the present invention are e.g. disclosed in WO 2007/095949, WO 2011/033021, WO 2013/127433, and PCT/EP2017/056059, the contents of which are all incorporated herein by reference.

OBJECT OF THE INVENTION

It is an object of embodiments of the invention to provide for improved agents for treatment of errors of metabolism. An object of other embodiments is to provide novel methods for preparing such improved agent. And, an object of yet other embodiments of the invention is to provide novel treatments of phenylketonuria (PKU), alkaptonuria, and hypertyrosinemia.

SUMMARY OF THE INVENTION

It has been found by the present inventor(s) that a carefully selected mixture of monomers and a target provides for MIPs with outstanding properties in terms of their binding capacity and specificity when the MIPs are purified according to the scheme disclosed herein. The MIPs obtained this way are believed to be novel chemical entities.

It has also been found by the present inventors that MIPs prepared using a Phe-containing template provide for a subpopulation of MIPs that surprisingly bind L-tyrosine (Tyr) with high affinity, meaning that one polymerization process surprisingly leads to two distinct products with very different but useful binding properties.

Finally, it has been found by the present inventors that the Phe-binding MIPs of the present invention have a binding capacity of such a magnitude that effective treatment of PKU in a standard adult person (70 kg) that ingests a diet containing recommended (by the authorities) amounts of protein can be attained by administration of less than 35 g MIP per day dependent on the proportional protein intake.

So, in a first aspect the present invention relates to a method for the preparation of molecular imprinted polymer (MIPs), which specifically bind L-phenylalanine (Phe), said method comprising the steps of
a) polymerization of a mixture comprising
2-methylprop-2-enoic acid (MAA),
1,4-bis(acryloyl)piperazine/1,4-diacryloylpiperazine (DAP), and
a template molecule consisting of L-Phe or a L-Phe derivative exposing a phenylalanine motif
in the presence of a catalyst and an oxidizing agent,
so as to obtain a cross-linked imprinted polymer,
b) if necessary (that is, if particle sizes after polymerization does not include a sufficient amount of MIPs having particle sizes smaller than 63µm) subsequently fragmenting the cross-linked imprinted polymer obtained in step a) to obtain a first fragmented polymer, and collecting the MIPs having particle sizes smaller than 63µm,
c) optionally washing and drying the polymer fraction obtained from step b,
d) fragmenting further the polymer fraction obtained from step c and collecting a second fragmented polymer having particle sizes in the range 150-250 nm,
e) subjecting second fragmented polymer obtained from step d to affinity chromatography where Phe constitutes the affinity tag (optionally as part of a larger molecule) in a chromatographic matrix, and
f) recovering MIPs binding to Phe in step e.

In a second aspect, the invention relates to a molecular imprinted polymer (MIP), which specifically binds L-phenylalanine (Phe), wherein said MIP is comprised of polymerized methacrylic acid (MAA) cross-linked with 1,4-diacryloylpiperazine (DAP).

In a third aspect, the invention relates to a composition comprising the MIP of the second aspect of the invention and embodiments thereof, said composition comprising a pharmaceutically acceptable carrier and/or diluent and/or excipient, wherein said composition is adapted for oral administration.

In a fourth aspect, the invention relates to a method for the preparation of MIPs, which specifically bind L-tyrosine (Tyr), said method comprising recovering MIPs that bind L-tyrosine from an initial composition of MIPs that have been prepared using, as the template molecule during polymerization and cross-linking, a molecule comprising at least one phenylalanine motif and comprising no Tyr residues.

In a fifth aspect, the invention relates to a molecular imprinted polymer (MIP), which specifically binds L-tyrosine (Tyr), wherein said MIP is comprised of polymerized methacrylic acid (MAA) cross-linked with 1,4-diacryloylpiperazine (DAP).

In a sixth aspect, the invention relates to a composition comprising the MIP of the fifth aspect of the invention and embodiments thereof, said composition comprising a pharmaceutically acceptable carrier and/or diluent and/or excipient, wherein said composition is adapted for oral administration.

In a seventh aspect, the invention relates to a method of treatment of phenylketonuria in a person in need thereof, said method comprising administering to a person in need thereof the MIPs according to the second aspect and embodiments thereof or the composition of the third aspect and embodiments thereof so as to deliver a daily effective dose of MIPs of the second aspect.

Finally, in an eighth aspect, the invention relates to a method for treatment of tyrosineamia and/or alkaptonuria, the method comprising administering to a person in need thereof
1) MIPs that bind phenylalanine, preferably the MIPs of the second aspect or the composition of the third aspect so as to deliver a daily effective dose of MIPs according to any one of claims; and/or administering
2) MIPs of the fifth aspect and embodiments thereof or the composition of the sixth aspect and embodiments thereof, so as to deliver a daily effective dose of MIPs of the fifth aspect and embodiments thereof.

LEGENDS TO THE FIGURE

FIG. 1: Effect of Phe binding MIP administration to PKU mice on Phe blood concentration. Each group contained 5 PKU mice, that were held on a phenylalanine restricted diet until start of the study. Each mouse was dosed 3 times a day for 2 days with either 20.7 mg protein per dosage or 20.7 mg protein per dosage plus Phe binding MIPs. A blood sample was drawn from each mouse prior to first dosage and 2 h after last dosage and analysed for phenylalanine. Three studies were performed with different dosages. Dotted lines/triangle data points represent measurements on animals receiving protein only; solid lines/square data points represent measurements on animals receiving both protein and Phe binding MIPs ("phelimin").

DETAILED DISCLOSURE OF THE INVENTION

Definitions

A "molecular imprinted polymer" (MIP) is a polymer comprising cavities (or voids) that at least in part correspond to one or more template molecules that have been incorporated in a monomer matrix including cross-linking monomers prior to polymerization. The resulting polymer after polymerization includes a number of cavities which correspond in shape to the template molecule. Typically the MIP is sequestered (fragmented, micronized) into small particles, thereby facilitating removal of template and leaving partial cavities open for interaction with a target molecule which resembles or is identical to the template molecule. In the present specification and claims, the term MIP generally refers to the particulate form of a MIP, meaning that the terms "MIP" and "MIPs" are used interchangeably with the expressions MIP particle and MIP particles, respectively.

It will be understood that the MIPs employed in the present invention are insoluble molecules/entities even though they may appear stable in suspension if sufficiently small. The MIPs are especially suitable as pharmaceutical for use in the gastrointestinal tract since their insolubility limits or prevents their passage into the body (e.g. into circulation) from the gastrointestinal tract. In other words, when administered orally, the MIPs used in the present invention will substantially remain confined to the gastrointestinal tract until they are disposed off in the faeces.

A "raw MIP" is a MIP which has not yet been subjected to affinity purification and hence contains a heterogenic mixture of MIPs with different binding characteristics, e.g. even MIPs with no ascertainable binding to the template molecule.

"Micronization" and "fragmentation" (used interchangeably) denote the process of sequestering MIPs which may still contain template into smaller particles. Any method suitable for this purpose may be used, cf. below.

A "target molecule" is in the present context any molecule or molecular motif to which a MIP can bind.

A "template molecule" is normally identical to the target molecule, but may also be a mimic thereof (i.e. a molecule having at least in part an identical 3D structure and profile which matches that of the target molecule—a mimic may for instance be constituted by a fragment of the target molecule or as in the present application by a larger molecule of which the intended target is an important part). The template serves as the "generator" of the voids in the MIP structure which subsequently are to be able to bind the target molecule.

A "phenylalanine-derivative where a phenylalanine motif is exposed" denotes a template molecule comprising a benzyl group, a phenyl ring or the benzyl group or phenyl ring combined with either a carboxylic group or an amino group. Therefore, any peptide containing phenylalanine (preferably di- or tripeptides) can be used as such a template molecule.

"Affinity purification" denotes any method for purification of a substance where specific binding between the substance and a binding partner is utilised. Many such methods utilise a capture agent bound to a solid support (such as a chromatographic matrix) which catches the substance. Typical examples known in the art are affinity purification using antibodies as capture agents coupled to chromatographic beads for purifying antigens that bind the antibody. It will be understood that the affinity purification methods applied according to the present invention are those which are capable of capturing suspended insoluble MIP particles having the sizes discussed herein.

A "solid phase" is in the present context any material which may be used to anchor a capture agent by means of covalent or non-covalent binding. Hence, any material (plastic polymers, sugars, metals, glass, silica, rubber etc) which is conventionally used in the preparation of chromatographic materials may serve as the solid phase. The solid phase material may contain suitable functional groups which allow coupling of the capture agent to the material in question. Such derivatized materials are known to the person of skill in the art of chromatographic purification of proteins and other macromolecules. Further, the solid phase may have any physical form which allows for capture of relatively large and insoluble particles such as MIPs (when comparing with single biomolecules such as proteins). Hence, the solid phase may be in the form of fibers (preferably hollow), a chromatography matrix, beads (preferably those that may be separated by electromagnetic means) or any other suitable form, cf. below.

When discussing sizes of MIPs herein, e.g. MIPs being smaller or larger than a given length X (e.g. 63μη), is herein meant that the size of the particles are such that they are capable or incapable of passing through sieves having a defined cut-off, i.e. diameter of the holes in the sieve X—the particles that pass through are "smaller than" X, and the particles that are retained are "larger than" X. In other words, a molecule may in theory be larger than 63μη along an axis, but still capable of passing through a 63μη sieve: in such a case, the molecule is said to be smaller than 63μη.

Certain abbreviations are used in the present disclosure: L-Phe denotes L-phenylalanine, Gly denotes glycine, Ala denotes either L-alanine, D-alanine, or a mixture of both, L-Asp denotes L-aspartic acid, Me denotes methyl, and OMe denotes O-methyl (—O—CH$_3$).

SPECIFIC EMBODIMENTS OF THE INVENTION

Embodiments Relating to the 1$^{st}$ Aspect of the Invention

As indicated above, the first aspect relates to a method for the preparation of molecular imprinted polymer (MIPs), which specifically bind L-phenylalanine (Phe), said method comprising the steps of
- a) polymerization of a mixture comprising
  - 2-methylprop-2-enoic acid (MAA),
  - 1,4-bis(acryloyl)piperazine (DAP), and
  - a template molecule consisting of L-Phe or a L-Phe derivative exposing a phenylalanine motif in the presence of a catalyst and an oxidizing agent, so as to obtain a cross-linked imprinted polymer,
- b) if necessary (due to large particle sizes) subsequently fragmenting the cross-linked imprinted polymer to obtain a first fragmented polymer and collecting the fraction thereof having particle sizes smaller than 63μm,
- c) optionally washing and drying the polymer fraction obtained from step b,
- d) fragmenting further the polymer fraction obtained from step c and collecting a second fragmented polymer having particle sizes in the range 150-250 nm,
- e) subjecting second fragmented polymer obtained from step d to affinity chromatography where Phe constitutes the affinity tag in a chromatographic matrix, and
- f) recovering MIPs binding to Phe in step e.

The polymerization mixture in step a preferably contains MAA and DAP in a MAA:DAP molar ratio of 5-30. Preferably, the ratio is between 6 and 27, such as between 7 and 24, 8 and 21, 9 and 18, and preferably between 10 and 15.

The exact polymerization method can vary. As will be clear from the examples, equally good results have been obtained using bulk polymerization followed by micronization step and using the reverse phase emulsion polymerization method in example 4. The latter method provides for MIP particles of such a generally small size that micronization in step b is not relevant, meaning that simple collection of sufficiently small polymer particles can be carried out directly in step b, see below.

The preferred molar ratio MAA:template molecule is between 1.0 and 4.0. Values can vary in this interval, meaning that the ratio can be selected from about 1.1, about 1.2, about 1.3, about 1.4, about 1.5, about 1.6, about 1.7, about 1.8, about 1.9, about 2.0, about 2.1, about 2.2, about 2.3, about 2.4, about 2.5, about 2.6, about 2.7, about 2.8, about 2.9, about 3.0, about 3.1, about 3.2, about 3.3, about 3.4, about 3.5, about 3.6, about 3.7, about 3.8, about 3.9, and about 4.0.

The template molecule is preferably an L-Phe derivative in the form of a peptide containing at least one L-Phe residue, which is a typical form of a L-Phe derivative exposing a phenylalanine motif. Good results have been obtained with L-Phe containing dipeptides or tripeptides, which are thus particularly preferred template molecules. Such di- or tripeptides can e.g. be selected from the group consisting of Gly-L-Phe (glycyl-L-phenylalanine), Ala-L-Phe, L-Asp-L-Phe-OMe, L-Asp-L-Phe, Gly-Gly-L-Phe, Ala-Gly-L-Phe, Gly-Ala-L-Phe, L-Phe-Gly, L-Phe-Ala, L-Phe-L-Phe, L-Phe-Ala-L-Phe, and L-Phe-Gly-L-Phe. A particularly preferred template molecule is Gly-L-Phe.

The catalyst in step a is typically selected from those that catalyse polyacrylamide gel polymerization in aqueous media. Useful catalysts are tetramethylethylenediamine (TEMED) and dimethylpiperazine. The preferred catalyst is TEMED. These catalysts typically have to be used together with a strong oxidizing agent. Hence, it is preferred that the oxidizing agent in step a) is selected from the group consisting of ammonium persulfate, potassium persulfate, and sodium thiosulfate, preferably ammonium persulfate (APS).

The fragmentation method utilised in step b is not essential, and is only applied if the particle sizes of the molecular imprinted polymers obtained from step a are too large. Essentially any method for downsizing of MIPs known in the art can be used: for instance, the fragmentation in step b can comprise grinding, milling, explosion, hammering, ball milling, cryo grinding, or collision homogenisation as well as any combination of these methods.

In order to ensure that the MIP particles obtained in step b) are smaller than 63μm, standard metal sieves with defined cut-offs can be used. For instance, it is preferred that the MIPs collected in step b have sizes in the 25-63μm range and this can be attained by utilising sieves with a 63μm cut-off, and collecting the MIPs that are able to pass through. Subsequently, sieves with a 25μm cut-off can be used, where the material retained is used in subsequent steps. However, since smaller particles can be subjected to the subsequent steps, step b need not isolate particles of any defined minimum size.

The optional washing is performed at alternating pH with an organic solvent, e.g. as shown in the examples. This ensures that accessible bound template is effectively removed prior to the following steps. One convenient way of washing the MIPs is to pack them in a column such as an HPLC column, thereby facilitating washing under elevated pressure with a solvent passing through the HPLC column.

Subsequent step d (the further fragmentation of MIP particles) is conveniently carried out in a ball mill or bead mill but as for step b the exact micronization method employed in inessential for the result to be achieved as long as the method is capable of providing a sufficient fragmentation. Hence, the methods recited above as convenient in step b are all relevant for the purposes of step d.

After step d, the MIP particles are now of such a small size that they remain in suspension for a prolonged time. To isolate/collect the MIPs in step d can hence be carried out by suspension of MIPs in a solvent (preferably an aqueous solvent such as water), subsequent incubation in an ultrasound bath (which can in its own right effect micronization), centrifugation, and isolation of the supernatant, which contains the 150-250 nm MIPs. Also, a washing step after step d and prior to step e can conveniently be carried out in order to remove any residual template, e.g. template that has been made accessible due to the further downsizing; this washing is typically carried out as a dialysis step, but also ultracentrifugation is a possibility—the washing step merely has to fulfil the purpose of separating MIPs and template.

The final step e and f resemble traditional chromatographic procedures carried out on truly soluble material: the affinity chromatography in step e) is conveniently carried out on a packed bed chromatographic column using a stationary chromatographic matrix, which carries the capture probe that includes Phe) and where the MIPs are suspended in a buffered aqueous solvent. Finally, the MIPs are recovered from the column by elution methods known per se. As shown in the examples, the preferred elution liquid is ethanol in water, such a 40% ethanol.

Embodiments Relating to the 2$^{nd}$ Aspect of the Invention

The molecular imprinted polymer (MIP) of the invention, which specifically binds L-phenylalanine (Phe), wherein said MIP is comprised of polymerized methacrylic acid (MAA) cross-linked with 1,4-diacryloulpiperazine (DAP), is believed to be a novel chemical entity.

The molar ratio between the MAA and DAP monomer residues is preferably between 5 and 30. However, the ratio is preferably between 6 and 27, such as between 7 and 24, 8 and 21, 9 and 18, and preferably between 10 and 15. In particular, it is preferred that this MIP of the invention is obtainable or obtained by the method of the first aspect of the invention.

As discussed above, the MIP of the second aspect and the MIP obtained by means of the method of the first aspect exhibit a very high binding capacity and affinity for its target, L-Phenylalanine. The MIP has a $K_D$ for binding to Phe of less than $10^{-7}$, but lower values have been measured: less than $10^{-8}$, less than $9 \times 10^{-9}$, less than $8 \times 10^{-9}$, less than $7 \times 10^{-9}$, less than $6 \times 10^{-9}$, less than $5 \times 10^{-9}$, less than $4 \times 10^{-9}$, less than $3 \times 10^{-9}$, and less than $2 \times 10^{-9}$. A preferred $K_D$ of about $10^{-9}$ has been measured with the L-Phe binding MIPs disclosed herein.

Embodiments Relating to the 3$^{rd}$ Aspect of the Invention

The composition of the 3$^{rd}$ aspect of the invention is prepared according to conventional formulation techniques. Since the active principle has an almost infinite shelf-life, the MIPs can be incorporated into any common oral dosage form: tablets, capsules, powders, granules, medicated gums, and suspensions, where all other ingredients (preservatives and other excipients) are standard choices.

However, in order to avoid problems with growth of fungi, bacteria or algae, a pharmaceutically acceptable disinfectant or preservative can be included in those formulations where such growth could present a problem.

The MIPs may also be formulated so that they are or can be incorporated into foods and drinks. Since it has turned out that the MIPs of the invention exhibit no taste, their inclusion in any kind of ingestible product has proven to be unproblematic.

For details of preparation of compositions of the invention for oral intake, reference is generally made to Remington's "Essentials of Pharmaceutics", Pharmaceutical Press 2012 (published 2013), ISBN 978 0 85711 105 0, in particular chapters 30, 31, and 32.

Embodiments Relating to the 4$^{th}$ Aspect of the Invention

As indicated above, it has surprisingly turned out the imprinting process described above in the first aspect of the invention provides for a sub-population of MIPs that are strong binders of the amino acid L-tyrosine. This is in spite of the fact that the template molecule Gly-L-Phe, which has been tested, does not include any Tyr functionality and in spite of the fact that MIPs obtained by the method of the first aspect (after purification) are highly specific for L-phenyl-alanine and e.g. binds significantly less to D-phenylalanine or approx. 700 times less effectively to L-Tyr. This evidences that preparation of "raw" MIPs from polymerization with a Phe-containing template provides for Tyr-binding MIPs also. So, the broadest embodiment of the 4$^{th}$ aspect relates as indicated above to a method for the preparation of MIPs, which specifically bind L-Tyrosine (Tyr), said method comprising recovering MIPs that bind L-Tyrosine from an initial composition of MIPs that have been prepared using, as the template molecule during polymerization and cross-linking, a molecule comprising at least one phenylalanine motif and comprising no Tyr residues. In particular, the template molecule is preferably a template molecule discussed in the context of the first aspect of the invention; as demonstrated in the Example section, this provides for a very effective imprinting process.

It is also preferred that the initial composition of MIPs is separated in at least 2 fractions, and recovering Tyr binding MIPs from a fraction, which is essentially free from MIPs that bind the Phe-containing capture probe—this may e.g. be accomplished by first separating the MIPs that bind L-Phe or Phe motifs with high affinity. The Expression "Phe motif" is in the present context typically meant a L-Phe residue such as an internal, N- or C-terminal Phe residue in a peptide or polypeptide.

So, a preferred embodiment entails the steps of
a) polymerization of a mixture comprising
  2-methylprop-2-enoic acid (MAA),
  1,4-bis(acryloyl)piperazine (DAP), and
  a template molecule discussed in the context of the first aspect of the invention (preferably Gly-L-Phe)
  in the presence of a catalyst and an oxidizing agent, so as to obtain a cross-linked imprinted polymer,
b) if necessary (cf. above) subsequently fragmenting the cross-linked imprinted polymer to obtain a first fragmented polymer and collecting the fraction thereof having particle sizes smaller than 63μm,
c) optionally washing and drying the polymer fraction obtained from step b,
d) fragmenting the polymer fraction obtained from step c and collecting a second fragmented polymer having particle sizes in the range 150-250 nm, and
e) subjecting the second fragmented polymer obtained from step d to affinity chromatography where
  e1) Tyr constitutes the affinity tag in a chromatographic matrix, or
  e2) Phe constitutes the affinity tag in a chromatographic matrix, recovering MIPs not binding to Phe, and subjecting the MIPs not binding to Phe to further affinity chromatography where Tyr constitutes the affinity tag (optionally as part of a larger molecule) in a chromatographic matrix, and
f) recovering MIPs binding to Tyr in step e.

As is clear from this embodiment, steps a-d are identical with steps a-d in the first aspect of the invention. Hence, all features relating to process parameters and reagents disclosed above for these steps of the first aspect of the invention apply mutatis mutandis to steps a-d of the 4$^{th}$ aspect.

Likewise, the remaining steps also can be carried out according to the general teachings provided above in respect of the first aspect. When the route e1 is selected, no step of removing Phe-binding MIPs is performed, so potentially the MIPs obtained this way may include Phe-binders—if route e2 is followed, the steps up to the Tyr affinity chromatography are identical with the steps prior to Phe purification in the first aspect, and all disclosures relating to these of the first aspect apply mutatis mutandis to the fourth aspect.

The final step e and f further resembles traditional chromatographic procedures carried out on truly soluble material: the affinity chromatography using Tyr as affinity tag in step e) is conveniently carried out on a packed bed chromatographic column using a stationary chromatographic matrix, which carries the capture probe that includes or is L-Tyr) and where the MIPs are suspended in a buffered aqueous solvent. Finally, the MIPs are recovered from the column by elution methods known per se. As shown in the examples, the preferred elution liquid is ethanol in water, such a 40% ethanol.

Embodiments Relating to the 5$^{th}$ Aspect of the Invention

It is believed that the molecular imprinted polymer (MIP), which specifically binds L-tyrosine (Tyr) described for the 5$^{th}$ aspect is a novel chemical entity. Its basic chemical composition is identical with that of the MIP of the second aspect of the invention, meaning that the molar ratio between MAA residues and DAP residues preferably is between 5 and 30. However, the ratio is preferably between 6 and 27, such as between 7 and 24, 8 and 21, 9 and 18, and preferably between 10 and 15. In particular, it is preferred that this MIP of the invention is obtainable or obtained by the method of the fourth aspect of the invention.

The $K_D$ values for binding between the Tyr-binding MIPs and L-Tyr are preferably of the same values as those discussed above for Phe-binding MIPs that bind to L-Phe.

Embodiments Relating to the 6$^{th}$ Aspect of the Invention

The composition of the 5$^{th}$ aspect of the invention is prepared according to conventional formulation techniques. Since the active principle has an almost infinite shelf-life, the MIPs can be incorporated into any common oral dosage form: tablets, capsules, powders, granules, medicated gums, and suspensions, where all other ingredients (preservatives and other excipients) are standard choices.

However, in order to avoid problems with growth of fungi, bacteria or algae, a pharmaceutically acceptable disinfectant or preservative can be included in those formulations where such growth could present a problem.

The MIPs may also be formulated so that they are or can be incorporated into foods and drinks. Since it has turned out that the MIPs of the invention exhibit no taste, their inclusion in any kind of ingestible product has proven to be unproblematic.

For details of preparation of compositions of the invention for oral intake, reference is generally made to Remington's "Essentials of Pharmaceutics", Pharmaceutical Press 2012 (published 2013), ISBN 978 0 8571 1 105 0, in particular chapters 30, 31, and 32.

Embodiments Relating to the 7$^{th}$ Aspect of the Invention

The MIPs of the second aspect, as well as the composition of the 3$^{rd}$ aspect of the invention are useful for treatment of diseases characterized by excess blood concentrations of L-Phe. As such a method of treatment of phenylketonuria in a person in need thereof, said method comprising administering to a person in need thereof the MIPs of the second aspect or the composition of the third aspect is provided. This method may e.g. be carried out as is generally disclosed in WO 2011/033021.

As discussed above, it is possible to control Phe in persons suffering from PKU by administering a feasible dosage per standard meal of the MIPs of the second aspect: an effective dose per meal is preferably 1-35 g/70 kg (I. e. 1-35 grams per 70 kg of bodyweight). Preferably, the effective dose per meal is at most or about 34 g/70 kg, such as at most or about 33, at most or about 32, at most or about 31, at most or about 30, at most or about 29, at most or about 28, at most or about 27, at most or about 26, at most or about 25, at most or about 24 at most or about 23, at most or about 22, at most or about 21, at most or about 20, at most or about 19, at most or about 18, at most or about 17, at most or about 16, at most or about 15, at most or about 14, at most or about 13, at most or about 12, at most or about 11, at most or about 10, at most or about 9, at most or about 8, at most or about 7, at most or about 6, at most or about 5, at most or about 4, at most or about 3, at most or about 3, and at most or about 2 g/70 kg. As shown in the examples, a dose per meal of about 11 g/70 kg bodyweight has until now been found to be effective.

So, a preferred range for the effective daily dosage (comprising 3 meals) is 3-105 g per 70 kg body weight, with more narrow dosage intervals being 20-45 g/70 kg, such as 25-40 g/70 kg, and 30-35 g/kg bodyweight. Hence, the daily effective dose may be about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, and about 105 g/70 kg.

As will be understood from the above, the MIPs are administered orally, typically as a suspension, as part of a food or drink, or as a solid formulation.

Embodiments Relating to the 8$^{th}$ Aspect of the Invention

In analogy to the 7$^{th}$ aspect is provided a method for treatment of tyrosineamia and/or alkaptonuria, the method comprising administering to a person in need thereof 1) MIPs that bind phenylalanine, preferably the MIPs of the second aspect and embodiments thereof or the composition of the 3$^{rd}$ aspect and embodiments thereof so as to deliver a daily effective dose of MIPs according to any one of claims of the second aspect; and/or 2) MIPs that bind tyrosine of the 5$^{th}$ aspect or the composition of the 6$^{th}$ aspect, so as to deliver a daily effective dose of MIPs of the 5$^{th}$ aspect and embodiments thereof.

In preferred embodiments, this is done as adjuvant therapy to nitisionone treatment of alkaptonuria, see below in Example 3.

As discussed above, it is possible to control Tyr in persons suffering from PKU by administering a feasible daily dosage of the Phe and/or Tyr binding MIPs: an effective dose is preferably 1-35 g/70 kg (I.e. 1-35 grams per 70 kg of bodyweight). Preferably, the daily effective does is at most or about 34 g/70 kg, such as at most or about 33, at most or about 32, at most or about 31, at most or about 30, at most or about 29, at most or about 28, at most or about 27, at most or about 26, at most or about 25, at most or about 24 at most or about 23, at most or about 22, at most or about 21, at most or about 20, at most or about 19, at most or about 18, at most or about 17, at most or about 16, at most or about 15, at most or about 14, at most or about 13, at most or about 12, at most or about 11, at most or about 10, at most or about 9, at most or about 8, at most or about 7, at most or about 6, at most or about 5, at most or about 4, at most or about 3, at most or about 3, and at most or about 2 g/70 kg.

So, a preferred range for the effective daily dosage is 10-15 g/70 kg, such as about 10, about 11, about 12, about 13, about 14 or about 15 g/70 kg.

As will be understood from the above, the MIPs are administered orally, typically as a suspension, as part of a food or drink, or as a solid formulation.

Example 1

Preparation of Phe Binding MIPs

Polymer is synthesized as a bulk polymer, also known as a monolith. The monomers, MAA (2-Methylprop-2-enoic acid, CAS no 79-41-4) and DAP (1,4-Bis(acryloyl)piperazine, CAS no 6342-17-2), as well as the template, the dipeptide Gly-L-Phe (GF), are dissolved in water in a glass tube and degassed by bubbling an inert gas through the solution. APS (ammonium persulfate, CAS No. 7727-54-9) and TEMED (tetramethylethylenediamine, CAS No. 110-18-9) are added and the glass tube is placed in a water bath at elevated temperature and left for polymerization overnight.

The glass tube is mechanically broken and the polymer, approx. 10 g, is collected and subject to a first down-sizing in a rotor mill. The down-sized polymer is sieved and the 25-63μη fraction is collected and washed thoroughly packed in an HPLC column under high pressure using alternating pH values and organic solvents.

The washed and dried polymer is then subject to a second down-sizing by ball-milling in a ball-mill with planetary motion. From the ball-milled sample a suspendable fraction is harvested by suspending the ball-milled polymer in water, incubate in an ultrasound bath and finally centrifuge. The supernatant contains a suspension of polymer particles with a size of approx. 150-250 nm. The polymer suspension is buffered with a 10×PBS buffer stock, pH 8.0, and is then ready for chromatography.

The suspension of polymer is applied to an affinity chromatography column, with PBS as running buffer, where Phe has been immobilized on the chromatography matrix as affinity tag. When the polymer sample has passed, the column is washed to remove polymer particles not tightly bound to the column and affinity captured polymer particles are subsequently eluted by changing the running buffer by including an organic solvent.

The eluted polymer particles are transferred into water or PBS by e.g. by dialysis or tangential flow filtration and concentrated before final formulation.

In a specific example, the entire general procedure was carried out as follows.

1. Pre-polymerization: 1.667 g Gly-L-Phe and 50 ml water is mixed and stirred in a 100 ml flask for 2 min and 1.301 g MAA is added. After 2 min of further stirring and 2 min in an ultrasound bath (Branson 2510) at room temperature (RT) in order to fully dissolve Gly-L-Phe, 38.834 g DAP is added. The flask is placed at 40° C. in a water bath with continued stirring for 5 min to achieve a homogenous solution. The flask is then left at RT for 1-2 h.

2. Polymerization: 17 ml of the pre-polymerization solution is transferred to a culture glass tube (25×150 mm) containing 100 mg APS, vortexed for 1 min (2,500 rpm) and placed in an ultrasound bath for 5 min. The solution is sparged for 5 min with argon, 75μι of a 25% solution in water freshly prepared TEMED is added and the tube is vortexed for 20 s at 2,500 rpm. The tube is closed with a tight cap and immediately placed at 70° C. in water bath and left for polymerization overnight.

3. Downsizing: The polymer is manually broken into approximately 1 cm pieces and subsequently milled in a rotor-mill (Fritsch Pulverisette 14) supplied with a 500 Tl sieving ring at 13,000 rpm.

The milled polymer is sieved (dry) through 63 and 25μιη stainless sieves for isolation of the 25-63μιη fraction. The isolated the 25-63μιη fraction is suspended in acetone and left for sedimentation for 5-10 min.

The supernatant is removed, and the suspension/sedimentation/decanting cycle is repeated until the supernatant appears clear. The settled polymer is dried overnight at 60° C. The dry polymer is packed into an HPLC column and washed under elevated (5-15 bar) pressure with the following solvents:

A. Ethanol/acetic acid 4:1 (vol/vol); 540 ml
B. Ethanol; 100 ml
C. Ethanol/NaOH (5M)/$H_2O$ 5:2:3; 200 ml
D. Ethanol; 100 ml
E. Ethanolacetic acid/$H_2O$ 18:1:1; 200 ml
F. Ethanol; 300 ml
G. Acetone; 100 ml The washed polymer is dried overnight at 60° C. and ball milled in a Fritsch Pulverisette 7 in a $ZrO_2$ milling chamber using $ZrO_2$ balls in two steps; using 1.5 mm balls in the first step and 0.5 mm balls in the final step. In both steps 5 g balls is placed in a 12 ml milling chamber and 1 g polymer is placed on top of the balls. Milling schedule is 30 min milling at 750 rpm, 30 min pause, 30 min milling at 750 rpm in reverse mode, etc. 10 cycles per step.

4. Harvest of a stable, suspendable fraction: After milling, the polymer is suspended in approximately 30 ml water, separated from the milling balls by a pipette, transferred to a 50 ml polypropylene centrifuge tube and placed in an ultrasound bath (Branson 2510) for approx. 30 min. After centrifugation at 4,500 G for 15 min the supernatant, around 25 ml, is harvested and contains a stable suspension of polymer particles with a size range of 150-250 nm. The absorbance at 254 nm in a 1 cm quartz cuvette is around 500-1,500 AU.

5. Preparation of sample for chromatography: The harvested fraction is dialyzed by Tangential Flow Filtration (TFF) using a Polyethersulfone filter with a 30.000 Dal cut off. The polymer suspension is subsequently buffered by 10×PBS (phosphate buffered saline) and diluted in 1×PBS (pH 8.0, 20 mM phosphate, 150 mM NaCl) to a final polymer concentration of 30 AU at 254 nm.

6. Isolation of Phe binding MIPs by affinity chromatography and work-up: The TFF'ed polymer is run on an affinity chromatography column (HiTrap® NHS-activated 5 ml column, GE Healthcare, 17-0717-01) coupled with Gly-L-Phe following the manufacturer's recommendations. 10 ml of the sample is passed through the column at 1 ml/min. The column is washed with additional 50 ml at 1 ml/min and the column is then eluted with 40% ethanol in water at 1 ml/min. The running buffer is PBS, pH 8.0. The eluted fraction of MIPs is dialyzed into water and concentrated by TFF and optional freeze dried.

Example 2

Isolation of Tyrosine (Tyr) Binding MIPs from the GlyPhe Chromatography Run-Through The run-through from the from the process for isolating Phe binding MIPs (affinity chromatography using a Gly-L-Phe coupled column) in step 6 in Example 1 is passed over a column (HiTrap® NHS-activated 5 ml column, GE Healthcare, 17-0717-01) coupled with Tyr following the manufacturer's recommendations. The same protocol is used as for running the Gly-L-Phe coupled column except that 20 ml sample (run through from the isolation of Phe binding MIPs) is applied. The column is washed with additional 50 ml at 1 ml/min and the column is then eluted with 40% ethanol in water at 1 ml/min. The running buffer is PBS, pH 8.0. The eluted fraction of MIPs is dialyzed into water and concentrated by TFF and finally freeze dried.

Surprisingly, this provides for isolation of high-capacity, high-avidity Tyr binding MIPs.

Patients suffering from either Tyrosinemia or Alkaptonuria and who are treated with nitisionone (CAS no 104206-65-7) are known to accumulate unhealthy amounts of tyrosine in the blood as a side effect of their treatment.

The only currently known remedy for this side effect is to prescribe a protein restricted diet. Since both Tyrosinemia and Alkaptonuria patients exhibit normal conversion of phenylalanine to tyrosine, i.e. the surplus of tyrosine is derived from dietary tyrosine as well as hydroxylated phenylalanine, a reduction in dietary phenylalanine uptake with Phe binding MIPs is considered beneficial for these patients. Furthermore, these patients should benefit from a reduction in dietary tyrosine by treatment with tyrosine binding MIPs in a manner analogous to the treatment of PKU patients with Phe binding MIPs.

Example 3

Establishing Human Doses of Phe-Binding MIPs in a Mouse Model

Each study group contained 5 PKU mice that were held on a phenylalanine restricted diet until start of the study.

Each mouse was administered 3 times a day over the course of 2 days with a dose of either 20.7 mg protein per dosage or 20.7 mg protein per dosage plus Phe-binding MIPs of the present invention.

A blood sample was drawn from each mouse prior to first dosage and 2 h after last dosage and analysed for L-phenylalanine. Three studies were performed with different dosages of Phe binding MIPs (see FIG. 1; dosages were 21, 18, and 13 mg MIP).

In a PKU mouse model (which is deficient in phenylalanine hydroxylase) is was found (FIG. 1C) that a ratio of Phe binding MIPs to protein ratio (w/w) of 0.63 (corresponding to 13 mg Phe binding MIPs per dose) neutralized the Phe from the protein administered to the mice, thus leading to a Phe concentration in the blood that was the same after 3 dosages per day for 2 days in the MIPs treated mice. On the other hand, mice receiving the same amount of protein, but no Phe-binding MIPs, exhibited an increase of Phe blood concentration of approximately 140μM over the course of the 2 day study.

If larger doses of Phe binding MIPs were administered to the mice, i.e. increasing the MIPs to protein ratio, the treated mice exhibited a decrease in blood Phe concentration after 2 days of treatment (FIGS. 1A and 1B)

If the MIPs to protein ratio from the mouse studies is transferred to human PKU patients it means that a standard meal (0.75 g protein/kg bodyweight/day) in a 70 kg person would require 11 g Phe Binding MIPs of the present invention to neutralize the Phe obtained from the dietary protein. In case the patient wants to decrease the blood Phe, but consume the same amount of protein, a higher Phelimin to protein ratio could be used.

Example 4

Industrial Scale Synthesis

Synthesis and processing of the polymers of the present invention in an industrial format, such as reverse phase emulsion polymerization, is typically performed through the steps described in the following example, which included the following steps:
1. Preparation of the aqueous phase
2. Preparation of the oil phase
3. Preparation of the W/O emulsion (mixing the aqueous and the oil phase)
4. Polymerization After the polymer synthesis, the polymer work-up is performed by washing steps to remove the oil phase from the polymer particles before the polymer continues into a diminution process by mechanical means in a bead mill.

Re 1. Preparations of the Aqueous Phase

The aqueous phase contains:

| Compound name | cas# | Amount (g) |
| --- | --- | --- |
| $H_2O$ | 7732-18-5 | 56.011 |
| DAP (1,4 diacryloylpiperazine) | 6342-17-2 | 48.535 |
| MAA (methacrylic acid) | 79-41-4 | 2.814 |
| APS (ammonium persulfate) | 7727-54-0 | 0.562 |
| Gly-Phe (H-Gly-L-Phe-OH) | 3321-03-7 | 3.755 |

Water and DAP was mixed to a macroscopically homogenous solution by simple stirring. Then MAA and Gly-Phe was added and dissolved at room temperature with stirring and ultrasound. The solution was filtered through a 1μη filter. Lastly, the APS was added to the filtered solution (99.173 g) and stirred until completely solubilized, i.e. for about 4 minutes.

Re 2. Preparation of the Oil Phase 139.98 g of isoparaffinic hydrocarbon solvent (Isopar M®, cas #64742-47-8) and 1.068 g surfactant (Hypermer® 6212, Croda Iberica SA) were mixed and the surfactant allowed to fully dissolve by stirring for 5-10 minutes.

Ad 3. Preparation of the W/O Emulsion 60 g of the aqueous phase was added to the oil phase (and sank to the bottom) in a cylinder glass and was then subjected to high shear stirring with an ultraturrax disperser (Heidolph Diax 900 at level 5) for 3 minutes after which a stable water-in-oil (W/O) emulsion was formed.

Ad 4. Initiation of the Polymerization

The emulsion was transferred to a two-necked reaction flask and degassed to a scheme of 3 iterations of vacuum (−0.8 bar vacuum) for 3 mins and argon flushing for 3 mins under stirring. Once degassed, 0.064 g TEMED (tetramethylethylene diamine, cas #110-18-9) was added and the emulsion heated to 70° C. in a water bath going from room temperature to 70° C. over a period of approximately 20-30 min. The resulting polymer (>90%) was in the form of 1-3μm, regular spherical particles. They were subsequently harvested by means of centrifugation (filtration or similar methods are equally well suited) and washed with ethanol and water using tangential flow filtration (TFF).

Work Up and Test of Polymer Particles from Reverse Phase Emulsion Polymerization.

The washed polymer beads were comminuted by wet bead milling using a Netzsch Labstar® equipped with a ceramic ($ZrO_2$) micro-chamber in two steps: first with 0.2 mm $ZrO_2$ beads followed by 0.1 mm $ZrO_2$ beads. The liquid phase was 50% ethanol in water adjusted to pH 10.0 with NaOH. After the final run, the average particle size was 170 nm determined by dynamic light scattering (Malvern Nanosizer®). The nanoparticles were washed using TFF and applied to an affinity chromatography column coupled with L-phenylalanine to test the phenylalanine binding properties. The nanoparticles from the reverse phase emulsion polymerization behaved similar to nanoparticles synthesized by bulk polymerization on the affinity chromatography.

The invention claimed is:

1. A molecular imprinted polymer (MIP), which specifically binds L-phenylalanine (L-Phe), wherein said MIP is comprised of polymerized methacrylic acid (MAA) cross-linked with 1,4-diacryloylpiperazine (DAP), and wherein said MIP has a $K_D$ for binding to L-Phe of less than $10^{-7}$ M, less than $10^{-8}$ M, less than $9\times10^{-9}$M, less than $8\times10^{-9}$M, less than $7\times10^{-9}$M, less than $6\times10^{-9}$ M, less than $5\times10^{-9}$M, less than $4\times10^{-9}$ M, less than $3\times10^{-9}$ M or less than $2\times10^{-9}$M.

2. The MIP according to claim 1, wherein the molar ratio between MAA residues and DAP residues is between 5 and 30.

3. The MIP according to claim 1, which is obtained by a method comprising the steps of
   a) polymerization of a mixture comprising
      2-methylprop-2-enoic acid (MAA),
      1,4-bis(acryloyl)piperazine (DAP), and
      a template molecule consisting of L-Phe or a L-Phe derivative exposing a phenylalanine motif in the presence of a catalyst and an oxidizing agent,
      so as to obtain a cross-linked imprinted polymer,
   b) if necessary subsequently fragmenting the cross-linked imprinted polymer to obtain a first fragmented polymer, and collecting the MIPs having particle sizes smaller than 63 μm,
   c) optionally washing and drying the polymer fraction obtained from step b),
   d) fragmenting the polymer fraction obtained from step b) or c) and collecting a second fragmented polymer having particle sizes in the range 150-250 nm,
   e) subjecting the second fragmented polymer obtained from step d) to affinity chromatography where Phe constitutes the affinity tag in a chromatographic matrix, and
   f) recovering MIPs binding to Phe in step e).

4. The molecular imprinted polymer according to claim 1, where the $K_D$ is about $10^{-9}$ M.

5. A composition comprising molecular imprinted polymers according to claim 1, said composition comprising a pharmaceutically acceptable carrier and/or diluent and/or excipient, wherein said composition is adapted for oral administration.

6. A method of treatment of phenylketonuria in a person in need thereof, said method comprising administering to a person in need thereof i) the MIPs according to claim 1 or ii) a composition comprising molecular imprinted polymers according to claim 1, said composition comprising a pharmaceutically acceptable carrier and/or diluent and/or excipient, wherein said composition is adapted for oral administration, so as to deliver a daily effective dose of MIPs according to claim 1.

7. The method according to claim 6, wherein the daily effective dose is 1-35 g per 70 kg body weight.

8. The method according to claim 7, wherein the effective dose per meal is at most or about 34 g/70 kg, such as at most or about 33, at most or about 32, at most or about 31, at most or about 30, at most or about 29, at most or about 28, at most or about 27, at most or about 26, at most or about 25, at most or about 24 at most or about 23, at most or about 22, at most or about 21, at most or about 20, at most or about 19, at most or about 18, at most or about 17, at most or about 16, at most or about 15, at most or about 14, at most or about 13, at most or about 12, at most or about 11, at most or about 10, at most or about 9, at most or about 8, at most or about 7, at most or about 6, at most or about 5, at most or about 4, at most or about 3, at most or about 3, and at most or about 2 g/70 kg.

9. The method according to claim 7, wherein the daily effective dose is 20-45 g/70 kg, such as 25-40 g/70 kg, and 30-35 g/kg.

10. The method according to claim 7, wherein the daily effective dose is selected from about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, and about 105 g per 70 kg body weight.

* * * * *

UNITED STATES PATENT AND TRADEMARK OFFICE
CERTIFICATE OF CORRECTION

PATENT NO. : 11,879,027 B2
APPLICATION NO. : 17/317033
DATED : January 23, 2024
INVENTOR(S) : Klaus Gregorius et al.

It is certified that error appears in the above-identified patent and that said Letters Patent is hereby corrected as shown below:

In the Claims

At Column 15, Claim 1, Lines 33-34, the text "$2\times10^-{_9}M$" should be changed to -- $2\times10^{-9}M$ --

Signed and Sealed this
Sixteenth Day of July, 2024

Katherine Kelly Vidal
*Director of the United States Patent and Trademark Office*